United States Patent [19]

Maurer

[11] Patent Number: 4,652,444
[45] Date of Patent: Mar. 24, 1987

[54] METHODS AND COMPOSITIONS FOR TREATING DENTAL STRUCTURES

[75] Inventor: Gerald L. Maurer, Cincinnati, Ohio

[73] Assignee: National Research Laboratories, Cincinnati, Ohio

[21] Appl. No.: 681,565

[22] Filed: Dec. 14, 1984

[51] Int. Cl.$^4$ .................... A61K 7/16; A61K 31/28; A61K 31/30

[52] U.S. Cl. .................................. 424/49; 514/494; 514/499; 514/501; 514/503; 514/505

[58] Field of Search ..................... 514/499; 424/49–58

[56] References Cited

U.S. PATENT DOCUMENTS

| | | | |
|---|---|---|---|
| 4,055,655 | 10/1977 | Maurer et al. | 514/494 |
| 4,146,608 | 3/1979 | Ritchey | 514/499 |
| 4,180,473 | 12/1979 | Maurer et al. | 514/499 |
| 4,278,610 | 7/1981 | Maurer et al. | 260/414 |
| 4,332,791 | 6/1982 | Raaf et al. | 514/499 |
| 4,339,429 | 7/1982 | Raaf et al. | 514/499 |

Primary Examiner—Shep K. Rose
Attorney, Agent, or Firm—Wood, Herron & Evans

[57] ABSTRACT

Novel methods and dental compositions for treating dental structures, such as teeth and subgingival structures, are disclosed. Uniquely, the dental compositions contain metal complexes which are characterized as having an unique aqueous proton induced dissociation property represented by a sigmoidally-shaped curve on a cartesian coordinate plot of the negative log of the metal ion concentration versus the negative log of the hydrogen ion concentration. This unique dissociation property enables the metal complexes to release therapeutic metal ions in the oral cavity for forming metal coordination complexes or salts within the dental structures. The formation of such complexes or salts within the dental structures is particularly effective and highly resistant to enzymatic degradation associated with microbial activity. Also, the metal ions of this invention are highly effective in inactivating the enzymes secreted by microbes in the oral cavity to further attenuate the disintegration process. The metal complexes of the new and vastly improved dental compositions advantageously are highly soluble yet readily dissociable at pH ranges normally encountered in the human mouth. As the active ingredient, the dental compositions contain a monometal complex of a multivalent heavy metal ion and a polyfunctional organic ligand in a ratio of about 1:1. An example of a dental composition employed is disodium monocopper(II) citrate in an amount of about 4 mg./ml., as copper, in a liquid vehicle having a pH of about 7.

10 Claims, 3 Drawing Figures

METHODS AND COMPOSITIONS FOR TREATING DENTAL STRUCTURES

BACKGROUND OF THE INVENTION

The normal flora of the oral cavity is composed of many types of aerobic, facultatively anaerobic and obligately anaerobic microorganisms represented by Streptococci and Actinomyces; Neisseria and Nocardia; Veillonella and Fusobacterium, respectively. The former are found almost exclusively on the oral mucosa; the latter two groups are found predominantly in subgingival (beneath the gum line) habitats. For instance Streptococci colonize the surfaces of the teeth secondary to plaque formation; plaque serves as a substrate, both in a mechanical sense and in a biological sense.

It is well known that mammalian teeth are vulnerable to degradation from the cariogenic manifestations of bacterial exudates, i.e., caries. Caries, in effect, result from the disintegration of tooth substance beginning at the exterior surface and progressing inwardly. Initially, the surface enamel of teeth, which is entirely non-cellular, is demineralized. Basically, this is attributed to the effect of acid products of either bacterial fermentation or saliva or both. Subsequent to the demineralization of the surface enamel, the dentin and cementum are decomposed generally from bacterial digestion of the protein matrix.

The essential first step in caries production appears to be due to the formation of plaque on the hard, smooth enamel surface of the dentition. Chitinoid structures are found bound tightly to the surfaces of mammalian dentition both supra and subgingivally in the form of plaque. Such plaque is highly resistant to chemical attack, being generally removable only by abrasive means, and can serve as a nutritional source for bacterial species. The essential second step in caries production appears to be due to the formation of large amounts of acid from either bacteria or saliva or both. Unfortunately, large concentrations of acid as aforesaid demineralize the adjacent enamel to initiate the formation of caries.

Plaque is often referred to as "bacterial plaque"; in fact, large numbers of bacterial species can be isolated from plaque deposits by usual culture techniques. Generally, it is theorized that plaque consists of a polymerized form of sialic acid, the origin of which is saliva. Sialic acids are acetyl derivatives of neuraminic acid. (These serve as monomers which, under conditions of acidified environments can easily polymerize). In the salt form, at basic pH ranges, they are relatively soluble, lending thixatropy to the saliva. Mucoid materials contain, often times, these and similar substances which give them a slippery feeling. Acid formed by bacterial activity on, for instance, carbohydrates tend to acidify the oral cavity to an abnormally low pH range. This tends to cause the neuramic acid derivatives to polymerize and there appears to be a chemical bond effected between the normal hydroxyapatite structure of the teeth and the polymerized neuraminic acid. Therefore, there exists a suitable enzymatic substrate in juxtaposition to a normal biological structure, a condition which can lead to the secondary enzymatic alteration of the desirable structure. Such activity is evidenced by caries formation.

It is well known that the periodic removal of plaque from dental enamel reduces the occurrence of caries. Furthermore, it is well known that the use of preparations containing available fluoride anions imparts anticaries protection to the dental surfaces, presumably by the insertion of fluoride ions into the structure of the hydroxyapatitie via substitution of or combination with the hydroxyl groups giving rise to the theoretical structures fluoroapatite or fluorohydroxyapatite. Such structures appear to be much less susceptible to the cariogenic activities of bacterial exudates which are composed of, among other entities, toxins and similar substances with enzymatic activity. That is, where such enzymatic activity might readily degrade the hydroxyapatite and its associated phosphate groups, the insertion of fluoride appears to render the structures far less susceptible to enzymatic degradation. Thus, caries formation is markedly reduced, as has been pragmatically documented, since the introduction of intentional water fluoridation and the use of dentifrices containing fluoride anions.

Therefore, there are two basic methods which are presently used concurrently as means to effectively reduce the formation of caries as a result of the activity from the normal bacterial flora present in the oral cavity. The first and less frequent method is a physical method which involves mechanical removal of the plaque from the surfaces of the teeth, since plaque is relatively resistant to chemical attack. The second and more frequent method is a chemical method to be conducted on a frequent or even daily basis which is concerned with chemically altering or mineralizing the normal hydroxyapatite structures of teeth to fluoroapatite or fluorohydroxyapatite with, for instance, fluoride containing dental compositions. Basically, the incorporation of fluoride into dental structures apparently renders teeth more resistant to enzymatic degradation thereby reducing the formation of caries.

In addition to the use of fluoride in aiding of the arrest of the caries process, several dental preparations have been heretofore formulated which have utilized divalent metals such as copper, chromium, cobalt and zinc as alternative dietary fortification means. Examples of such dental preparations can be found in U.S. Pat. Nos. 4,375,460, 4,339,429, 4,332,791, 4,235,633, 4,048,300 and 2,154,168. Unfortunately, the divalent metal complexes disclosed in the above listed U.S. patents and incorporated into those dental preparations have been generally heretofore unsatisfactory. For instance, virtually all of those divalent metal complexes presently utilized are relatively insoluble in aqueous media. In addition to the disadvantage of insolubility, such divalent metal complexes are so stable at the pH ranges generally encountered in the oral cavity that only slight amounts of metal ions dissociate rendering them relatively ineffective. Moreover, because of the stability factor, generally larger quantities of the divalent metal complexes have to be incorporated into those dental preparations which adversely affect the overall taste and mouth feel of the final products.

With respect to the subgingival structures, this situation differs somewhat in that anaerobic bacterial flora appear to preferentially attack soft tissue vis-à-vis the apatite components. Periodontal ligaments bind the tooth to the bony structure of the jaws not unlike the ligamentous structures associated with the normal musculoskeletal junctures. These periodontal ligaments appear to be highly susceptible to enzymes secreted by the anaerobic species found subgingivally. The gradual decomposition of both the ligamentous and bony structures eventually leads to the ultimate loss of attachment of the teeth to the bone. This unfortunately can result in sinus tract infection, subgingival and pericoronal abscess formation and ultimate tooth loss.

In summary, previous attempts or approaches have been made to formulate suitable dental compositions for mineralizing teeth to prevent or reduce caries. Heretofore no satisfactory dental compositions other than those containing fluoride anions have been developed which can overcome the problems aforementioned. Basically, the types of known divalent metal complexes fall into two undesirable categories: those in which cations are normally found very tightly bound to counter ions, and those found in an insoluble form as hydrous oxides of the metal.

In other words, all of the dental compositions utilizing divalent metal complexes other than fluoride provided hitherto invariably necessarily lack some of the key fundamental properties required to provide sufficient amounts of therapeutic metal ions in the oral cavity. Consequently, there are strong dental and commercial needs for dental compositions containing metal complexes suitable for mineralizing dental structures to reduce or prevent the decay of dental structures.

SUMMARY OF THE INVENTION

In brief, the present invention seeks to alleviate the above-mentioned problems and shortcomings of the present state of the art through the discovery of novel dental compositions and methods of use thereof for treating dental structures, such as teeth and subgingival structures to reduce or prevent decay and decomposition thereof. A particular class of metal complexes has now been found especially suited for making available metal ions, such as copper, to prevent or reduce the degenerative process of the dental structures. Broadly, the invention comprises the application in the oral cavity of an effective amount of a 1:1 metal complex of a multivalent heavy metal ion bound to a polyfunctional organic ligand. In one preferred form to assist in the application of the metal complexes, they are dispersed in a suitable aqueous vehicle to formulate a desired dental composition. The 1:1 metal complex has an aqueous proton induced dissociation property represented by a sigmoidally-shaped curve on a cartesian coordinate plot of the negative log of the metal ion concentration versus the negative log of the hydrogen ion concentration. It is found that the 1:1 metal complexes having such a dissocation property provide unique means to provide copper ions to the dental structures for treating disorders of the same.

The multivalent heavy metal ions may include, for instance, bismuth, chromium, cobalt, copper, zinc and the like, and preferably copper, whereas the polyfunctional organic ligand can be derived from, for example, the class of alpha or beta hydroxy polycarboxylic acids, such as citric acid, as well as functionally substituted acids, such as alpha or beta amino, sulfhydro, phosphinol and the like. In particular disodium-, dipotassium-, or dilithium- monocopper(II) citrate are especially suitable for formulating the dental compositions of this invention. In addition, a suitable buffer may be incorporated into the dental composition which may include, for example, citric acid, for adjusting pH.

Therefore, the new and vastly improved dental compositions and methods of this invention for treating dental structures provide novel means for preventing caries and decomposition of subgingival structures. Remarkably, the nature of the 1:1 metal complexes employed in the dental compositions is such that they make readily available metal ions to mineralize the dental structures by the formation of metal coordination complexes or salts therein. The formation of such complexes or salts within the dental structures is particularly effective and highly resistant to enzymatic degradation associated with microbial activity in the oral cavity. Also, the metal ions are highly effective in inactivating enzymes secreted by the microbes present in the oral cavity as a further means to reduce the degenerative process of the dental structures associated with such enzymes.

In another feature of the present invention, it is directed to unique advantages in connection with the 1:1 metal complexes employed in the dental compositions. For instance, the 1:1 metal complexes are highly soluble yet easily dissociable to make available metal ions for mineralizing the dental structures and/or inactivating enzymes secreted by microbes at the pH ranges generally encountered in the oral cavity. This is particularly illustrated in the application of this invention where metal ions are required to be introduced into the subgingival structures in large amounts. Since the pH range in the mouth is about 4 to about 9 and generally at about 7, copper ions of this invention are made available at the pH encountered in the mouth. The invention therefore contemplates providing the release of large amounts of metal ions from the soluble metal complexes at a pH of about 7, because of their relative instabilities at about pH 7. These preferred 1:1 metal complexes are very stable, even at high alkaline pHs, and relatively inert to organic moieties. Yet, by reason of the unique dissociation property as demonstrated by a sigmoidally shaped behavior on a pM-pH diagram, these 1:1 metal complexes offer desired release of metal ions at a pH wherein degeneration of dental structures, such as subgingival structures, occurs. Thus, the present invention provides an unique system for making therapeutical metal ions abundantly available to dental structures in the form of formulated dental compositions containing soluble, easily dissociable metal ions. It is therefore a feature of the present invention to provide improvements in the art by increasing the availability of metal ions in the oral cavity for mineralizing dental structures and/or inactivating enzymes secreted by microbes normally present in the oral cavity.

In a further feature, the dental compositions of the present invention may be formulated into different types of preparations, such as solids, liquids, gels or pastes and include, toothpastes, dental creams, or dental gels, tooth powders, liquid dentrifices, tablets, mouthwashes and the like. In addition, the dental compositions may contain a suitable thickener, abrasive agent, flavor and/or sweetener to assist in formulating a desired final product.

Thus, it can be appreciated that the special features and unique advantages of the dental compositions and methods of use of this invention make the same highly effective for treating various dental structures to combat the undesirable degenerative processes associated with the normal bacterial flora present in the oral cavity.

It is acknowledged by the inventor herein that his U.S. Pat. Nos. 4,055,655, 4,129,509, 4,180,473 and 4,278,610 disclose the metal complexes and methods of making same. The metal complexes have now been found especially surprisingly effective for mineralizing dental structures according to the present invention.

However, even though such complexes were reported as effective anti-microbial agents and metal transport agents, it had not been previously known that they may be uniquely effective in dental compositions for treating dental structures. Furthermore, such findings and other advantages of the present invention as described herein are considered unexpected and unobvious.

The above and other features and advantages of the invention, including various novel details of the methods and types of dental compositions used therewith, will now be more particularly described with reference to the detailed description and pointed out in the examples, figures and claims. It should be understood that the methods and dental compositions embodying the invention are shown in the example by way of illustration only and not as a limitation of the invention. The principles and features of this invention may be employed in various and numerous embodiments without departing from the scope of the invention.

DETAILED DESCRIPTION OF THE INVENTION

Figure 1:
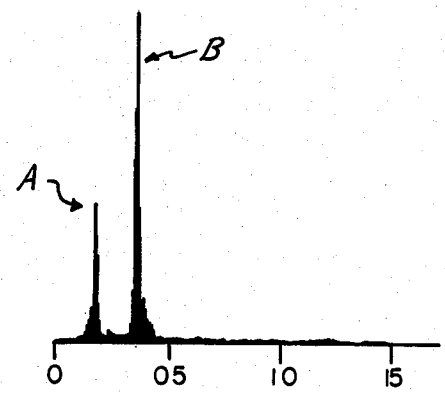

By way of illustrating and providing a better appreciation of the present invention, the following detailed description and examples are given concerning methods and dental compositions of this invention for mineralizing dental structures and/or inactivating enzymes secreted by microbes.

In a presently preferred form, the dental compositions of this invention comprise a monometal complex of a multivalent heavy metal and a polyfunctional organic ligand in a ratio of 1:1 of the heavy metal to the ligand, the complex having a dissociation property represented by a sigmoidally shaped plot on a pM-pH diagram. Specific examples of the metal complex are dialkali metal monocopper(II) citrates represented by disodium-, dipotassium- or dilithium- monocopper(II) citrate. These dialkali monocopper(II) citrates have a dissociation property represented by a sigmoidal plot, wherein the curves of two directions meet at a point within the pH range of about 7 to about 9. It has been established that these dialkali monocopper(II) citrate complexes in basic media, on the order of about pH 9 to about pH 12, are very stable, i.e., have an effective stability constant, $K_{eff}$ of the order of about $10^{12}$ to about $10^{13}$. However, $K_{eff}$ of these dialkali monocopper-(II) citrate complexes at a pH of about 7 to about 9 are on the order of about $10^5$ to about $10^{12}$. Therefore, at a pH of around 7, the effective stability constant of the monocopper(II) citrate complex is considerably lower (a thousand to several hundreds of thousand times lower) and a significant free $Cu^{++}$ concentration is available for mineralizing dental structures. For example, about 10% of the copper in the complex is in the ionized state at or about pH 7 while approximately 0.1% of the copper is ionized at or about pH 9.

Thus, it is to be understood that the dental complexes of this invention are sensitive to pH, and as the pH is lowered to or below about 7, then more copper ions are made available. In general, the metal complexes will tend to dissociate over a pH range of about 3 to about 12. Above about pH 12, the complexes tend to be destroyed by the alkaline media, precipitating from the media as hydrous metal oxides. Below about pH 7, the instability of the metal complex results in high concentrations of the free $Cu^{++}$ upon demand, as explained to effect treatment of the dental structures. Since the pH of the oral cavity in for example, human mouths, varies within wide limits which are typically between about 4 and about 9, the release of metal ions is most effective. The complexes will preferably be dispersed in a vehicle to provide a composition having a pH from about 4 to about 9 and preferably about 7 to maximize release of the metal ions in the oral cavity for treatment.

In accordance with this description and a presently preferred embodiment, it will become apparent that other metal complexes of polyfunctional organic ligands respond to the model of this invention where they exhibit the dissociation property characterized by a sigmoidal curve on a standard pM-pH diagram. For example, based upon the monometal-polyfunctional organic ligand complex of this invention, other metal ions of a monovalent or multivalent nature, specifically, divalent and polyvalent cations including zinc, nickel, chromium, bismuth, silver, cobalt, and especially copper, as well as other similar and suitable metallic or heavy metal cations may be employed. Other polyfunctional organic ligands may be substituted for the citric acid specifically exemplified by a preferred embodiment of this invention. Included among other polyfunctional ligands are the broader class of alpha or beta hydroxy polycarboxylic acids into which class the citric acid falls. Also, other functionally substituted acids such as alpha or beta amino, sulfhydro, phosphinol, etc. can be substituted in the molecular model of the metal complex of this invention and similar results can be achieved. In general, from a metal complex formula standpoint, the monometal complex of copper and citric acid corresponds to either of the following structural forms (A) and (B).

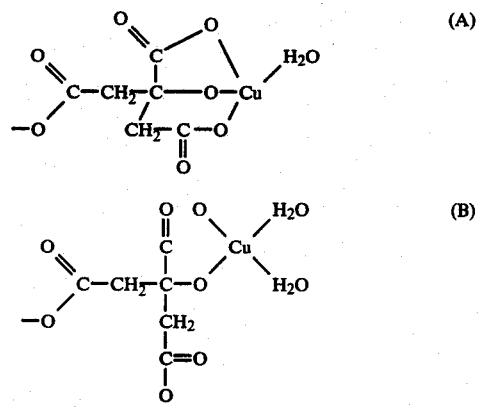

The (A) form is believed to be the preferred form by applying free energy considerations. A single proton introduced into the complex structure represented by either form (A) or (B) prevents deformation of stable five- or six- member coordinate rings. With the introduction of a proton, only seven-member rings may be formed by the coordination of the acetate electron donors and such seven-member ring structures are unstable. Therefore, the complex molecule dissociates and presents metal ions for mineralizing dental structures.

The (A) and (B) structural forms may be more generally represented by the following models;

MODEL (A)

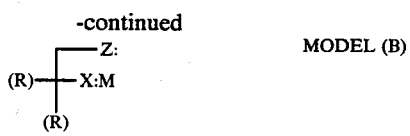

MODEL (B)

In the above models, the solid line segments represent a chemical bond between elements in the skeletal structure of the molecules; X, Y, and Z represent electron pair donors; (R) represents any elemental or molecular species or groups; M represents a metal and wherein the proton affinity of X is greater than that of Z, Y, or R. It will, therefore, be appreciated that other Lewis based proton pairs, and other metal ions, may be substituted into these structural models for oxygen, divalent copper, or, for that matter, the carbon atoms to provide a molecular model which will similarly dissociate upon the introduction of one proton or similarly behaving species as exhibited by the sigmoidal behavior on a pM-pH diagram. The molecular models are thus alternative expressions for the complexes of this invention.

The unusual steric configuration of the molecules of these copper complexes imparts to it a dipole nature which is characterized by the solvation of water at either pole in a rather rigid, highly polarized manner. This characteristic allows the hydrated complex to electrostatically adsorb to the surfaces of finely divided particles possessing either electronegative or electropositive surface characters. It also permits the "shielded" copper in the complex to migrate intact through membranes such as cell walls of microbes. While no present direct evidence of intact transport has been obtained, all collective results enable one to inductively reason that such transport occurs. The result is that the complex containing the metal ion can travel into areas which otherwise exclude similar compounds. For example, the application of copper salts to a proteinaceous membrane results in the attachment of the copper ions to the membrane components as in the formation of copper proteinates or salts. Little if any of the copper ion, in a soluble, ionized, yet available state progresses far beyond the oral cavity.

Referring to the background of this invention, divalent metal complexes have been incorporated into dental preparations, but because metal ions in those complexes are very tightly bound and/or shielded from the acceptor site, the metal ions are essentially unavailable to perform very useful functions, biochemically speaking. In contrast, the unique proton induced dissociation of complexes of this invention renders metal ions, such as copper ions, to be made readily available as follows:

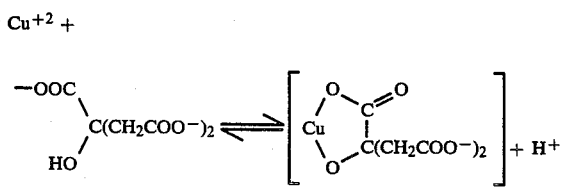

In addition, then, to the dipolar character of the 1:1 copper complex of this invention, it exhibits, most importantly, a relatively weak formation constant ($K_f$) meaning that the copper acceptors with stronger $K_f$ values can remove the copper ion from the 1:1 copper complex. This is accomplished in vivo by such structures as free amino acid groups, sulfhydryl radicals, hydroxyapatite in dental structures and any Lewis acid which can react with the coordination bonds holding the copper in place. That is, insertion of a hydrogen ion into the system can replace the displaced hydrogen ion originally associated with alcoholic hydroxyl group of the citrate moiety, thereby destabilizing the complex. Hence, the complex is characterized by possessing a proton induced dissociation character. This property is important in the pharmocodynamics of the copper complex of this invention and its use in the treatment of dental structures.

As used herein, the term "dental structures" is meant to include those structures located in the oral cavity, such as teeth and subgingival structures, which are subject to, for instance, enzymatic disintegration as a result of enzyme secretion by microbes present therein. By the term "subgingival structures", it is meant herein to include structures located below the gum line such as roots, peridontal ligaments and bony structures. By the term "disorders", it is meant to include, but is not limited to, plaque and calculus formation, caries, bad breath, and dental structure degradation.

Therefore, in accordance with the present invention, it is directed to providing novel dental compositions and methods for treating dental structures in animals. The compositions and methods are particularly useful in controlling plaque formation and decay of dental structures due to, for instance, the destructive enzymatic activity of enzymes secreted by microbes on such structures. This is accomplished, for instance, by enzyme inactivation or mineralization of the dental structures with the dental compositions of this invention. Further, the compositions and methods are useful in controlling calculus accumulation on teeth particularly when applied, for instance, routine prophylactically. Thus, the metal complexes of the invention can be advantageously utilized, for example, in the prevention of caries and the accumulation of calculus on teeth, and in attenuating the decomposition of subgingival structures, such as periodontal ligaments.

To accomplish the above, the 1:1 metal complexes are applied to the above mentioned structures in the oral cavity to make available metal ions, such as copper ions, (CuII), to mineralize the dental structures by the formation of metal coordination complexes or salts with the hydroxy and fluoroapatite. For example, the formation of cupricapatite in the dental structures provides complexes that are particularly effective and highly resistant to enzymatic degradation. Further, such mineralized structures are less susceptible to the undesirable formation of plaque and calculus thereon. More importantly, the periodontal ligament structures are uniquely derivatized by virtue of such copper complex formation on the surface of the fibrils available to the otherwise destructive enzymatic activity of the subgingival bacterial species.

With respect to the pH of the human mouth, it generally varies within wide limits typically ranging from about 4 to about 9, as aforesaid, and normally it is about 7. Thus, in order for the metal ions to be made available for the formation of complexes and salts of various structural anionic ligands and/or counter ions, the metal ions should be presented in a form which permits solubility and dissociation in the pH range of the oral cavity. The 1:1 metal complexes of this invention, and especially those of copper and citrate, are uniquely suited to provide such substances. Thus, high levels of soluble yet easily dissociable metal complexes are available for mineralizing the dental structures via this unique transport system.

In addition to the formation of complexes and salts which are resistant to enzymatic attack, the metal complexes of this invention provide metal ions, such as copper, which readily inactivate a host of enzymes which can decompose dental structures. In this manner, the otherwise destructive enzymatic degradation of, for instance, the teeth and periodontal structures is effectively attenuated. Even in the absence of complete attenuation of all susceptible substrates, the dental compositions of this invention are advantageously suited for retarding the rate of the destructive enzymatic activity presently associated with the enzymes secreted by the microbial flora present in the oral cavity. Thus, the incorporation of the 1:1 metal complexes, which provide readily available metal ions, such as copper ions (II), into the dental compositions of this invention can be advantageously utilized by both the dental practitioner and the patient as a means to combat dental decay.

In a further feature of the present invention, it is found that when the dental structures, such as teeth, are treated with the 1:1 copper complex plaque or calculus formation thereon is substantially reduced. Such unique results assist in the reduction or inhibition of caries production.

Further, the dental compositions particularly when formulated into liquid dentifrices or mouthwashes can be employed as deodorizers or breath fresheners to substantially reduce bad breath generally associated with the microbes present in the oral cavity.

Normal intact soft tissue usually shows no reaction, as evidenced by discoloration, in the presence of the copper complexes of this invention. On the other hand, abraded, infected and otherwise macerated tissue as well as granulation tissue might exhibit slight to moderate blue-green discoloration. This is presumably due to the greater number of available coordination sites in the tissues undergoing either rapid degeneration or rapid regeneration.

In preparing a preferred dental composition, the amount of the copper complex incorporated into the composition should be in the range from about 0.05% up to about 5%, by weight, calculated on the copper ion of the total composition. Preferably, the range is from about 0.1% to about 1% of copper and most preferably from about 0.2% to about 0.4% of copper.

Types of 1:1 copper complexes particularly suitable for supplying copper ions in accordance with this invention are dialkali metal monocopper(II)citrates represented by, for example, disodium-, dipotassium-, or dilithium- monocopper(II) citrates and especially disodium- monocopper(II)citrate as aforesaid.

In addition to the metal complexes, the dental compositions may contain other suitable compounds, such as thickeners and abrasive agents. The preferred thickener may be derived from the various cellulose derivatives, such as carboxymethylcellulose. The amount of thickener incorporated into the dental compositions may widely vary, for instance, from about 1% to about 10% depending upon the type of composition being manufactured. For instance, if the dental composition is formulated into a viscous liquid the amount of thickener may be added in a lesser sutable amount than if it is formulated into paste. Thus, in one instance, the dental compositions of this invention may be formulated into, for instance, a liquid, cream, or paste depending upon the amount of thickener being incorporated therein.

As to the abrasive agents, most suitable in this respect are, for example, aluminum oxide, aluminum hydroxide, talc, pumice, dicalcium phosphate and the like. The amount of these abrasive agents may vary and is generally from about 10% to about 50% by weight of the dental compositions. It should be understood, however, that the incorporation of a suitable abrasive is not an essential feature of the invention. Nevertheless, it is found that when an abrasive agent is incorporated into the dental compositions, they advantageously provide a scratching effect on the dental structures, such as the tooth enamel, providing a more suitable surface for the metal ions to complex with.

Also, in the dental compositions, any suitable flavoring or sweetening agent may be employed in formulating a flavor for the compositions of the present invention. Exemplary of suitable flavoring constituents may include, for instance, the flavoring oils, e.g., oils of spearmint, peppermint, wintergreen, sassafras, clove, sage, eucalyptus, marjoram, cinnamon, lemon, and orange, as well as other suitable flavors. Suitable sweetening agents include sucrose, lactose, maltose, sorbitol, sodium cyclamate, saccharin, aspartame, etc. In formulating the compositions, the flavoring and sweetening agents may together constitute for example from about 0.01% to about 1% or more of the composition.

The dental compositions should have a pH practicable for use. A pH range from about 4 to about 9 is particularly desirable and more preferable is about 7. The reference to the pH is meant to be the pH of the dental composition. If desired, any suitable substance may be added to adjust the pH, such as citric acid.

It should be understood that the above dental compositions may be varied in many particulars. For instance, the preparation of the various ingredients in each product prepared may be varied to a considerable degree so far as their character and relative weight ratio is concerned, and also so far as the physical character of the method of compounding is concerned, depending upon the particular physical character of the product desired. The specified combinations of ingredients may be used in any suitable preparation designed for application for the oral cavity, which preparation is referred to herein as a dental composition. Such dental compositions may be in solid, liquid, gel or paste form and include toothpaste, dental creams or dental gels, toothpowders, liquid dentrifices, tablets, mouthwashes and the like. Such products can be prepared in the usual manner. In the preparation of toothpowders, it is usually sufficient to mechanically admix the various solid ingredients. It is to be understood, of course, that the various ingredients may be wholly or in part substituted by other suitable ingredients having similar chemical or physical or physiological properties.

With respect to the dental cream, gel or paste compositions, the liquids and solids should be suitably proportioned to form an extrudible mass having a desired consistency. The consistency, however, should be suitable for use in an extrudible tube typically lined with, for example, aluminum or lead or in a pressurized container.

Exemplary of a preferred dental liquid composition of this invention includes in suitable amounts aluminum hydroxide, dicalcium phosphate, sorbitol, carboxymethylcellulose and water, in addition to the 1:1 copper complex. Preferably, the 1:1 copper complex is in an amount which provides approximately 4 milligrams per milliliter of copper. With this concentration, 5 drops of the liquid composition would contain about 1 milligram of copper in the form of the 1:1 copper complex. Thus, for application purposes, since about 1 milligram of copper is approximately the recommended daily allowance for an adult, it is suggested that at least about 5 drops of such a dental liquid composition be used in an application. It should be understood that, while it is not recommended, even if swallowed inadvertently that amount of copper is innocuous.

In using the dental compositions of this invention, it is suggested that a regimen of treatment with such a composition consists of at least once per day treatment with application via any suitable dental instrument, such as a softbristled brush, which has the capability of subgingival penetration with minimal trauma. In addition, the 1:1 metal complexes of this invention may be applied professionally by, for instance, a dentist or dental hygienist utilizing conventional equipment. For example, the 1:1 metal complexes may be applied routine prophylactically to teeth via a rubber prophylaxis cup to reduce or prevent plaque or calculus accumulation as well as caries formation. Before application, however, it is preferred to first scale the teeth with, for example, a hand pick and/or an ultrasonic scaler to provide a clean surface.

The inventor's U.S. Pat. Nos. 4,278,610, 4,180,473, 4,129,509 and 4,055,655 disclose methods for the preparation of the 1:1 metal complexes and methods for the determination of dissociation of such complexes which are suitable for use in the dental compositions and methods of this invention. The entire contents of these U.S. patents are incorporated herein by reference.

PREPARATION OF THE METAL COMPLEXES AND DENTAL COMPOSITIONS

The following methods were employed to prepare the compositions of this invention. In the following examples, disodium-monocopper(II) citrate (MCC) was employed. This copper citrate complex (MCC product) was made as follows:

INGREDIENTS:

65 ml water
65 gms citric acid, anhydrous
35 gms basic copper carbonate [$CuCO_3.Cu(OH)_2.H_2O$]
60 gms sodium bicarbonate ($NaHCO_3$)

The citric acid was dissolved in the water. The basic copper carbonate was added with stirring and dispersed well. This mixture was allowed to react for approximately 10 minutes or until the foam ($CO_2$ generation) subsided. Sodium bicarbonate was added slowly with gentle mixing until the pH was between 5.5 and 6.0. The solution was mixed until a black granular precipitate was no longer visible [$Cu(HCO_3)_2$]. The remainder of the sodium bicarbonate was added slowly with gentle stirring to adjust the pH to 7.0 for storage. The soluble copper chelate was thus prepared free from a second salt. A disodium-monocopper(II) citrate(MCC) product was prepared having a concentration of 100 mg of copper, by weight, per ml.

Other techniques for making the complexes are set forth in my U.S. Pat. No. 4,278,610, column 5, lines 65–68 and column 6, lines 1–57 and incorporated herein by reference.

In order to formulate MCC into liquids, creams, gels, pastes and the like, it was necessary to be very critical in the choice of ingredients. MCC was found to be chemically incompatible with many substances. As developed above, the compositions of this invention must also provide a pH which will not deleteriously affect the activity of the complex. Unique and advantageous formulations for a paste and liquid vehicle to be utilized with the metal complexes of this invention were found to satisfy the chemical demands and incompatibility problems of the metal complexes, e.g., MCC, as well as the aesthetic requirements as follows:

| PASTE VEHICLE | |
|---|---|
| Dibasic calcium phosphate | 50 gms. |
| Aluminum hydroxide gel | 20 gms. |
| Sorbitol | 5 gms. |
| Carboxymethylcellulose | 3 gms. |
| Peppermint oil | 0.1 gms. |
| Water | 21.9 gms. |
| | 100 gms. |

The above ingredients were all combined and intimately mixed to generate a smooth and homogeneous paste. To the paste, 4 mls. of the above-prepared MCC product, which contained 100 mg. of copper by weight per ml., was thoroughly mixed with 100 gms. of the paste vehicle. An MCC toothpaste having approximately 4 mg. of copper, by weight, per gram of toothpaste resulted.

LIQUID VEHICLE AND MCC DENTAL PRODUCT

To 100 mls of the above-prepared MCC product containing 100 mg of copper by weight per ml., a sufficient amount of dipotassium hydrogen phosphate (approximately 0.5% by weight of liquid) was added to maintain the pH at about 7. The resultant liquid represented a liquid MCC dental product.

It should be understood, however, that a solid form of copper citrate may be substituted for the liquid MCC product described above to prepare the MCC dental products of this invention.

EXAMPLE I

Several human teeth, having been extracted for therapeutic purposes, were immersed in a 100% ethanol bath for two weeks to accomplish dehydration of the pulp cavities and to preserve the integrity of the tooth structures. While formalin solution is routinely utilized for preservation purposes, formaldehyde is a well known reducing agent which may cause alteration or reduction of the copper(II) species by mechanisms other than the native mechanisms. Therefore, absolute ethanol was substituted for formalin since it is a satisfactory substitute and is also commonly employed for the purpose of preserving biological specimens.

The determination of the presence of copper within the tooth structures was conducted with electron microscopy coupled with energy dispersion analysis by X-ray (EDAX) since this method offers evidence of the presence or absence of a number of atoms in a structure, especially surface structures. Further, because of the high vacuum employed in this procedure, dehydration of the tissue was essential thereby requiring the ethanol treatment described above.

Upon subjecting the dehydrated tissue to electron microscopy coupled with EDAX, no macroscopic changes in appearance were noted in the teeth so processed. Organic material was seen to adhere to the root areas of the teeth. Under the scanning electron microscope (SEM), the crystalline structures were easily seen in the root area. SEM-EDAX was performed in these areas which were devoid of visible soft tissue residues at 40,000X. Only the crystalline material was studied.

Since the cementum is the component immediately adjacent to the bony structure of the jaw, it was determined inadvisable to attempt to scrape or otherwise remove the cementum layer from the underlying dentin since this would present a less natural condition for study. Cementum represents a comparable degree of calcification and hardness to the bone. The primary differences between enamel, dentin and cementum are the amounts of calcium hydroxyapatite component. Additionally, cementum contains a higher amount of collagen than either the dentin or the enamel, thereby offering more potential binding sites for copper ions than the crystalline material of the enamel.

Because the treated teeth exhibited adequate conductivity, direct SEM examination was conducted without the use of sputtered gold or other coatings.

Figure 2:
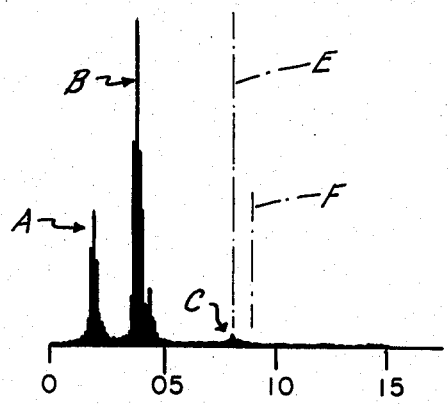
Figure 3:
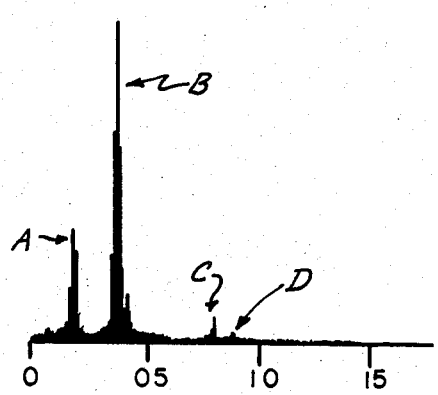

FIGS. 1-3 are drawings of the EDAX spectra of three different areas of a tooth treated by first washing with distilled water, drying with a tissue and then applying a liquid dental composition, which was prepared as described above, containing approximately 4 milligrams per milliliter of disodium monocopper(II) citrate using a soft-bristled brush. The process was repeated on six different teeth with the same results.

More specifically, FIGS. 1-3 represent various EDAX displays of three areas of the same tooth. A right lower central incisor was treated with the liquid dental composition from the mid-line to the anatomical right. The balance of the facial aspect of the tooth was not treated. A portion of the tooth was exposed to the liquid dental composition containing about 4 milligrams per milliliter of the active ingredient, disodium- monocopper(II) citrate. A light brushing action was used on the enamel surface for a period of about 30 seconds; a cotton swab containing the disodium monocopper(II) citrate was employed to bathe the subgingival structures for a period of about 30 seconds. After treatment, the tooth was washed in copious amounts of tap water and dried with a tissue.

FIG. 1 illustrates the untreated enamel. Clearly visible are the peaks due to the phosphorus designated by arrow A and calcium designated by arrow B. The major calcium peak was due to the K-alpha electron emission while the minor peak was due to K-beta electron emission. No other element was visible or observed.

FIG. 2 illustrates the treated surface of the same tooth and clearly reveals a K-alpha peak for copper designated by arrow C indicating that copper had been inserted into the tooth structure. As aforesaid, arrow A represents phosphorus whereas arrow B depicts calcium. In addition, the computer-generated marking system utilized to identify the location of the K-alpha and K-beta peaks for copper has been incorporated into this figure and are designated as E and F, respectively.

FIG. 3 reveals phosphorus as designated by arrow A and calcium as designated by arrow B of the dentin and cementum together with both a K-alpha and K-beta peak for copper as designated by arrow C and D, respectively, indicating that a larger amount of copper had been introduced into the cementum tissue than in the enamel.

EXAMPLE II

This is an example of a series of cases of patients who have been confirmed as heavy calculus formers that were treated with a metal complex disclosed by this invention. Generally, the medication utilized was composed of the active ingredient, disodium monocopper-(II) citrate (MCC), C.A.S. Registry Number: 65330-59-8, dispersed in an aqueous vehicle comprising aluminum hydroxide, dicalcium phosphate, sorbitol, carboxymethylcellulose and water to form a paste. All of the cases incorporated herewith, as an example, were confirmed diagnostically by a dentist employing the usual examining techniques, i.e., physical examination, etc. The ages of the patients who participated in this example ranged from 35 to 73 years.

All of the patients in this example, prior to their treatment with the metal complexes of this invention, had self-treated. In self-treating, all patients brushed with a standard dentifrice, flossed, and applied a mixture of baking soda, salt and water to their teeth at least once a day to contain or control calculus build up. Subsequent to and in conjunction with self-treatment, each patient received professionally a standard course of therapy which involved routinely scaling the teeth with a hand pick and an ultrasonic scaler and polishing the teeth mechanically with a mixture of pumice and stannous fluoride via a rubber prophylaxis cup. The patients in this example were treated every 3, 4 or 6 months and the length of standard treatment by the dentist ranged from about 4 years to about 12 years.

At the time of the first examination by the dentist, each patient's mouth was in extremely poor condition, and gross calculus build up was observed; however, no caries or restorations were present. After initiating standard professional therapy, the condition of each patient's mouth showed signs of only slight improvement with a minor reduction in calculus accumulation.

Subsequent to the standard professional therapy, treatment of all sides of the six lower front teeth with MCC was initiated and performed by the dentist every 3, 4 or 6 months for a total of 10 months. Treatment consisted of first scaling the six lower front teeth with a hand pick and an ultrasonic scaler to debride the teeth and then polishing the teeth mechanically with the above described MCC mixture via a rubber prophylaxis cup. After instituting therapy with the copper complex of this invention, the patients all experienced a dramatic reduction in calculus accumulation on the six lower front teeth as compared to the remaining teeth which were treated with the standard therapy. The overall appearance of the six lower front teeth was excellent. The patients experienced no side effects or tissue irritation or had any major complaints. Two patients, however, complained of a metallic taste from the MCC mixture which subsided immediately upon rinsing. For a more detailed presentation of this example, see the following table.

TABLE

| Patient | Sex | Race | Age | History | | Cond. of Mouth at First Exam | Calculus Accumulation | | | |
|---|---|---|---|---|---|---|---|---|---|---|
| | | | | Yrs. of Treatment by Dentist | Recall Freq. for Treatment by Dentist | | Condition of Mouth after Receiving Standard Therapy | Amt. of Calculus at First Exam | Amt. of Calculus after Receiving Standard Therapy | Amt. of Calculus after Application of MCC |
| 1 | F | C | 70 | 12 years | Every 3 mths. | +2 | +6 | +2 | +4 | +8 |
| 2 | F | C | 37 | 6 years | Every 4 mths. | +2 | +8 | +3 | +6 | +9 |
| 3 | F | N | 73 | 4 years | Every 6 mths. | +1 | +4 | +1 | +3 | +8 |
| 4 | F | C | 61 | 5 years | Every 6 mths. | +3 | +5 | +2 | +3 | +7 |
| 5 | F | C | 35 | 8 years | Every 6 mths. | +1 | +7 | +1 | +6 | +9 |

The only teeth treated with the MCC were all sides of the lower six front teeth.
The remaining teeth in the mouth were treated with the standard therapy.
History code - 1 = poorest condition
10 = best condition
Calculus Accumulation code - 1 = worst condition
10 = best condition (total absence of accumulation)

Thusly, it can be seen from the Examples that the dental compositions and methods of use in accordance with the invention are effective in treating and mineralizing dental structures including teeth and subgingival structures. As a result, the dental compositions of this invention provide unique means heretofore unavailable for making available metal ions in the oral cavity for reducing or preventing decay of and calculus accumulation on dental structures.

The present invention may, of course, be carried out in other specific ways than those herein set forth without departing from the spirit and essential characteristics of the invention. The present embodiments are, therefore, to be considered in all respects as illustrative and not restrictive, and any changes coming within the meaning in equivalency range of the appended claims are to embraced therein.

What is claimed is:

1. A method of reducing calculus accumulation on scaled teeth as well as treating dental disorders including bad breath, caries, dental structure degradation, and plaque formation which comprises applying to said scaled teeth structures (1) by mechanically polishing them for a sufficient amount of time an effective amount of a dental composition containing as the active ingredient a monometal complex of metallic tasting copper as a multivalent heavy metal ion and a polyfunctional organic ligand in a ratio of 1:1 said metal ion to said ligand selected from the group consisting of an organic acid and a substituted organic acid, said complex having an aqueous proton induced dissociation property represented by a sigmoidally-shaped curve on a cartesian coordinate plot of the negative log of the metal ion concentration versus the negative log of the hydrogen ion concentration, and a therapeutically acceptable aqueous vehicle for said active ingredient for releasing metal ions at a pH range of from about 4 to about 9 to treat said dental disorders and (2) rinsing until the metallic taste subsides.

2. The method of claim 1 wherein said metal complex is copper complexed with an alpha hydroxy polycarboxylic acid.

3. The method of claim 2 wherein said complex is dialkali metal monocopper(II) citrate.

4. The method of claim 1 wherein said substituted organic acid selected from the group consisting of hydroxy polycarboxylic, amino polycarboxylic, sulfhydro polycarboxylic, and phosphenol polycarboxylic.

5. The method of claim 1 wherein said vehicle is selected from the class consisting of an aqueous liquid, aqueous cream, aqueous gel or an aqueous paste.

6. The method of claim 5 wherein said vehicle comprises in suitable amounts an abrasive, sweetener, thickener and water.

7. The method of claim 6 wherein said vehicle comprises aluminum hydroxide, dicalcium phosphate, sorbitol, carboxymethyl cellulose and water.

8. The method of claim 3 wherein said dialkali metal monocopper(II) citrate is from about 0.05% by weight to about 5% by weight of said composition.

9. The method of claim 1 wherein said composition comprises disodium monocopper(II)citrate in an amount of about 0.4% by weight in an aqueous vehicle comprising aluminum hydroxide, dicalcium phosphate, sorbitol, carboxymethylcellulose and water.

10. The method of claim 1 wherein the dental composition is applied to the dental structures via a toothbrush.

* * * * *